(12) United States Patent  (10) Patent No.: US 8,664,271 B2
Borgeat  (45) Date of Patent: Mar. 4, 2014

(54) STABILIZED LEUKOTRIENE B$_4$ (LTB$_4$) AGENT PHARMACEUTICAL FORMULATION

(75) Inventor: Pierre Borgeat, Sillery (CA)

(73) Assignee: LTB4 Sweden AB, Stockholm (SE)

( * ) Notice: Subject to any disclaimer, the term of this patent is extended or adjusted under 35 U.S.C. 154(b) by 1260 days.

(21) Appl. No.: 11/231,359

(22) Filed: Sep. 20, 2005

(65) Prior Publication Data

US 2006/0063837 A1  Mar. 23, 2006

Related U.S. Application Data

(60) Provisional application No. 60/610,962, filed on Sep. 20, 2004, provisional application No. 60/635,009, filed on Dec. 13, 2004, provisional application No. 60/635,482, filed on Dec. 14, 2004.

(51) Int. Cl.
*A61K 31/202* (2006.01)

(52) U.S. Cl.
USPC .................................... 514/560; 514/456

(58) Field of Classification Search
None
See application file for complete search history.

(56) References Cited

U.S. PATENT DOCUMENTS

| | | | |
|---|---|---|---|
| 4,568,559 A * | 2/1986 | Nuwayser et al. | 427/2.15 |
| 4,786,505 A * | 11/1988 | Lovgren et al. | 424/468 |
| 5,780,055 A * | 7/1998 | Habib et al. | 424/464 |
| 5,789,441 A * | 8/1998 | Gosselin et al. | 514/560 |
| 6,093,741 A | 7/2000 | Gosselin et al. | 514/560 |
| 2004/0132820 A1 | 7/2004 | Gosselin et al. | 514/560 |

FOREIGN PATENT DOCUMENTS

| | | |
|---|---|---|
| EP | 0 179 959 A1 | 5/1986 |
| WO | WO 97/29751 | 8/1997 |
| WO | WO 98/24397 | 6/1998 |
| WO | WO 03/004054 A1 | 1/2003 |
| WO | WO 03/105823 A1 | 12/2003 |

OTHER PUBLICATIONS

Hammarstrom, "Leukotrienes." Anual Review of Biochemistry 1983: 52;355-377.*
Samuelsson_"The discovery of the leukotrienes." Am J Respir Crit Care Med 2000:161;S2-S6.*
Berry et al. *J. Biol. Chem.*, 278(27):24449-24460 (2003).
Tsikas et al. *Fresenius J. Anal. Chem.*, 347:376-381 (1993).
Wynalda et al. *Anal. Chem.*, 54:1079-1082 (1982).

* cited by examiner

*Primary Examiner* — Walter Webb
(74) *Attorney, Agent, or Firm* — Mintz Levin Cohn Ferris Glovsky and Popeo, P.C.; Ivor R. Elrifi; Matthew Pavao, J.D.

(57) ABSTRACT

The present invention relates to a novel pharmaceutical formulation comprising an LTB4 agent at an alkaline pH effective to stabilize the LTB4 agent and provide a formulation with an increased shelf-life. The formulation of the present invention has an increased shelf-life of at least 24 months.

13 Claims, 11 Drawing Sheets

LTB$_4$ agents at 35 µg/ml

STABILIZED LEUKOTRIENE B₄ (LTB₄) AGENT PHARMACEUTICAL FORMULATION

RELATED APPLICATIONS

This application claims priority to U.S. Ser. No. 60/610,962 filed Sep. 20, 2004, U.S. Ser. No. 60/635,009 filed Dec. 13, 2004, and U.S. Ser. No. 60/635,482 filed Dec. 14, 2004, each of which is incorporated herein by reference in its entirety.

BACKGROUND OF THE INVENTION (a) Field of the Invention

The invention relates to a novel $LTB_4$ agent pharmaceutical formulation of an alkaline pH effective to stabilize the $LTB_4$ agent and provide a formulation with an increased shelf-life. Thus, the invention relates to a composition comprising an $LTB_4$ agent and a pharmaceutically acceptable carrier at an alkaline pH.

(b) Description of Prior Art

Leukotriene $B_4$, itself, is a twenty carbon tetraunsaturated fatty acid and is a relatively unstable molecule. Isotonic aqueous solutions of $LTB_4$ at pH 7.0-7.6, which are suitable for administration to humans and animals are stable for only short periods of time (weeks to months) when stored at temperatures ranging from 2° C. to 25° C. (and above 25° C.). Indeed, $LTB_4$ agents are subject to oxidation, isomerization of double bounds ($LTB_4$ contains two cis and two trans double bounds), racemization ($LTB_4$ contains two chiral centers), esterification ($LTB_4$ contains a carboxylic group), lactonization, among various possible structural alterations.

Although $LTB_4$ agents have a great pharmaceutical utility, their use as therapeutic agents in animals or human is problematic, because of their insufficient stability and shelf-life in solution at temperatures between 2° C. to 25° C.

The scientific literature indicates that until presently, $LTB_4$ formulations for administration to humans and animals are aqueous solutions at pH 7.0-7.5 which are stored at very low temperatures (−20° C. or below) to avoid degradation. Alternatively, $LTB_4$ is used as ethanolic solutions, also stored at low temperature to avoid degradation, which are diluted with a (pH 7.0-7.5) buffer or evaporated to dryness and redissolved in a (pH 7.0-7.5) buffer immediately prior to use. Such formulations are inadequate for the use of $LTB_4$ as a therapeutic agent in humans and animals (unpractical and short shelf-life).

Given the potential of $LTB_4$ agents as a therapeutic agents for the prophylaxis and treatment of infections and cancer in humans and animals, it would be highly desirable to provide with a novel $LTB_4$ agent pharmaceutical formulation of an alkaline pH effective to stabilize the $LTB_4$ agent and provide a formulation with an increased shelf-life.

SUMMARY OF THE INVENTION

One aim of the present invention is to provide with a novel $LTB_4$ agent pharmaceutical formulation of an alkaline pH effective to stabilize the $LTB_4$ agent and provide a formulation with an increased shelf-life.

In accordance with one embodiment of the invention there is provided an $LTB_4$ agent pharmaceutical formulation, comprising a therapeutically effective amount of an $LTB_4$ agent, a salt thereof, an ester thereof, or an ether thereof in association with a pharmaceutically acceptable carrier at an alkaline pH effective to stabilize the $LTB_4$ agent, thereby increasing the formulation shelf-life. Thus, the invention relates to a composition comprising an $LTB_4$ agent, a salt thereof, an ester thereof, or an ether thereof and a pharmaceutically acceptable carrier at an alkaline pH.

In accordance with another embodiment of the present invention, the preferred alkaline pH ranges between 7.1 and 14, more preferably between 7.5 and 10.5. Preferably the pH is above 7.6, more preferably between 7.7 and 11.5. Even more preferably the pH is above 8.1, such as between 8.2 and 14, especially between 8.5 and 12.5, such as between 8.5 and 11.5, most preferably between 9.5 and 11.5, such as about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, or 11.5. In another preferred embodiment, the preferred alkaline pH ranges between 8.0 and 9.0, between 8.5 and 9.5, between 9.0 and 10.0, between 9.5 and 10.5, or between 10.0 and 11.5. In one embodiment, a preferred pH range is between 9.5 and 10.5.

In some embodiments, the $LTB_4$ agent pharmaceutical formulation comprises a therapeutically effective amount of an $LTB_4$ agent in association with a pharmaceutically acceptable, alkaline reacting carrier. Wherever the present application describes an embodiment relating to a pharmaceutically acceptable carrier at an alkaline pH effective to stabilize the pharmaceutical formulation in question, this embodiment also includes a pharmaceutically acceptable, alkaline reacting carrier.

In accordance with another embodiment of the present invention, the carrier is an aqueous carrier.

In accordance with another embodiment of the present invention, the carrier is a particulate solid coated with an alkaline matrix or constituted of an alkaline matrix, and the carrier may be selected from the group comprising organic solvents or a mixture thereof and water.

In accordance with another embodiment of the present invention, the stabilized formulation comprises water and at least 50% (vol/vol), preferably at least 60% (vol/vol), more preferably at least 70% (vol/vol), such as about 75% (vol/vol), especially at least 80% (vol/vol) of a co-solvent. In a particular embodiment of the invention, the stabilized formulation comprises water and 1 to 49% of a co-solvent or water and 50 to 99% of a co-solvent. Said co-solvent may be selected from the group consisting of ethanol, propyleneglycol, polyethylene glycol, isopropyl alcohol, benzyl alcohol, propanediol, glycerol, glycofurol, dimethylsulfoxide, dimethylacetamide, and mixtures thereof. In a particular embodiment of the present invention, the stabilized formulation comprises at least 90% (vol/vol) of said co-solvent.

In accordance with another embodiment of the present invention, the formulation is in a liquid form or in a freeze-dried form or in a crystalline form or in a solid amorphous form, preferably in a liquid form or in a freeze-dried form. Most preferred formulations are aqueous liquids or solids (whether freeze-dried or crystallized).

In accordance with another embodiment of the present invention, the aqueous carrier is selected from the group comprising water, alkaline metal hydroxide solutions, such as sodium hydroxide solution, buffered saline solutions, such as Phosphate Buffered Saline (PBS), co-solvent-containing aqueous solution, such as alcohol-containing aqueous solution, sugar solutions, or a mixture thereof. Said co-solvent-containing aqueous solution typically contains from about 1% to about 49% (vol/vol) of co-solvent.

In accordance with another embodiment of the present invention, the co-solvent present in the co-solvent-containing aqueous solution is selected from the group consisting of ethanol, propyleneglycol, polyethylene glycol, isopropyl alcohol, benzyl alcohol, propanediol, glycerol, glycofurol, dimethylsulfoxide, dimethylacetamide, and mixtures thereof.

In accordance with another embodiment of the present invention, the formulation is stabilized at a temperature ranging from −25° C. to 45° C., preferably from 0° C. to 40° C., such as 2° C. to 35° C., especially 5° C. to 25° C., when the carrier is an aqueous carrier and the formulation is in a liquid form, and a temperature ranging from −25° C. to 45° C., preferably from −20° C. to 40° C., more preferably −10° C. to 30° C., especially 0° C. to 20° C., most preferably 0° C. to 10° C., when the carrier is an organic carrier, such as an alcohol-containing carrier, or the formulation is in a freeze-dried form. Other most preferred temperature ranges, when the carrier is an organic carrier, such as an alcohol-containing carrier, or the formulation is in a freeze-dried form are −20° C. to 0° C., such as −10° C. to 0° C., or 20° C. to 40° C., such as 20° C. to 30° C.

In accordance with another embodiment of the present invention, the formulation further comprises a chelating agent or a pharmaceutically acceptable salt of a chelating agent thereof in an amount effective to stabilize the $LTB_4$ agent.

Preferred chelating agents in accordance with another embodiment of the present invention include, without limitation, the following:

an aminopolycarboxylic acid,
ethylenediaminetetraacetic acid (EDTA), diethylenetriaminepentaacetic acid (DTPA), nitrilotriacetic acid (NTA), glutamic acid, and aspartic acid,
EGTA, and
DTPA.

In accordance with another embodiment of the present invention, the pharmaceutically acceptable salt may be selected from a group consisting of the salts of sodium and potassium ions.

In accordance with a particular embodiment of the present invention, the stabilized formulation may be further stabilized in the freeze-dried form by comprising Human Serum Albumin (HSA) in the formulation.

In accordance with another embodiment of the present invention, the chelating agent is present in amounts of from about 0.001 to about 1.0 percent by weight of the $LTB_4$ agent formulation, more preferably the chelating agent is present in amounts of from about 0.01 to about 40 percent by weight of the $LTB_4$ agent formulation.

Preferred $LTB_4$ agents in accordance with the present invention include, without limitation, the following:
leukotriene $B_4$[5S,12R-dihydroxy-6,8,10,14(Z,E,E,Z)-eicosatetrae-noic acid] ("$LTB_4$")
$LTB_4$, 14,15-dihydro-$LTB_4$ ("$LTB_3$"), 17,18-dehydro-$LTB_4$ ("$LTB_5$"), 19-hydroxy-$LTB_4$, 20-hydroxy-$LTB_4$, and 5(S)hydroperoxy and 5-deoxy analogs thereof,
5(R)-hydroxy and 5(R)-hydroperoxy analogs of the $LTB_4$ agent,
leukotriene $A_4$ ("$LTA_4$"), 14,15-dihydro-$LTA_4$ ("$LTA_3$"), and 17,18-dehydro-$LTA_4$ ("$LTA_5$"),
14,15-dihydro-$LTA_4$ methyl ester and $LTB_4$ methyl ester,
5(S)-hydroxy-6,8,11,14(E,Z,Z,Z)-eicosatetraenoic acid ("5-HETE"), 14,15-dihydro-5-HETE, 17,18-dehydro-5-HETE, and 5(R)-hydroxy, 5(S)-hydroperoxy, 5(R)-hydroperoxy analogs thereof,
leukotrienes $C_4$ and $D_4$ and 14,15-dihydro or 17,18-dehydro analogs thereof; N-acyl or N-alkyl derivatives of leukotrienes $C_4$ and $D_4$ and 14,15-dihydro or 17,18-dehydro analogs thereof, 5,12-dihydroxy-6,8,10,14-eicosatetraenoic acid, 5-hydroxy-6,8,11,14-eicosatetraenoic acid and isomers thereof,
20,20,20-trifluoromethyl-$LTB_4$; 19-methyl-$LTB_4$, 19,19-dimethyl-$LTB_4$, 19-fluoro-$LTB_4$, 19,19-difluoro-$LTB_4$, 18,20-difluoro-$LTB_4$, and 20-fluoro-$LTB_4$,
3-thio-$LTB_4$, 3-hydroxy-$LTB_4$, 3-methyl-$LTB_4$, 3,3-dimethyl-$LTB_4$, 3-fluoro-$LTB_4$, 3,3-difluoro-$LTB_4$, and 2,3-difluoro-$LTB_4$, $LTB_4$ methylsulfonylamide, $LTB_4$ methylamide, 1-tetrazole $LTB_4$, and
a salt thereof, an ester derivative thereof and an ether derivative thereof.

Particularly preferred, $LTB_4$ agents in accordance with the present invention are selected from the group consisting of $LTB_4$, $LTB_3$, $LTB_5$, 20-hydroxy-$LTB_4$, 20,20,20-trifluoromethyl-$LTB_4$, 19-hydroxy-$LTB_4$, 18-hydroxy-$LTB_4$, 3-hydroxy-$LTB_4$, 2-hydroxy-$LTB_4$, 4-hydroxy-$LTB_4$, 5-deoxy analogs thereof, and salts, esters or ethers thereof.

Even more preferred, $LTB_4$ agents in accordance with the present invention are selected from the group consisting of $LTB_4$, $LTB_3$, $LTB_5$, 20-hydroxy-$LTB_4$, 20,20,20-trifluoromethyl-$LTB_4$, 3-hydroxy-$LTB_4$, 5-deoxy analogs thereof, and salts, esters or ethers thereof.

The LTB4 agent is preferably present in amounts of from about 0.1 μg/ml to 25 mg/ml of the formulation, preferably 1 μg/ml to 25 mg/ml of the formulation, more preferably from about 1 μg/ml to 1 mg/ml of the formulation.

DETAILED DESCRIPTION OF THE INVENTION

Figure 1:
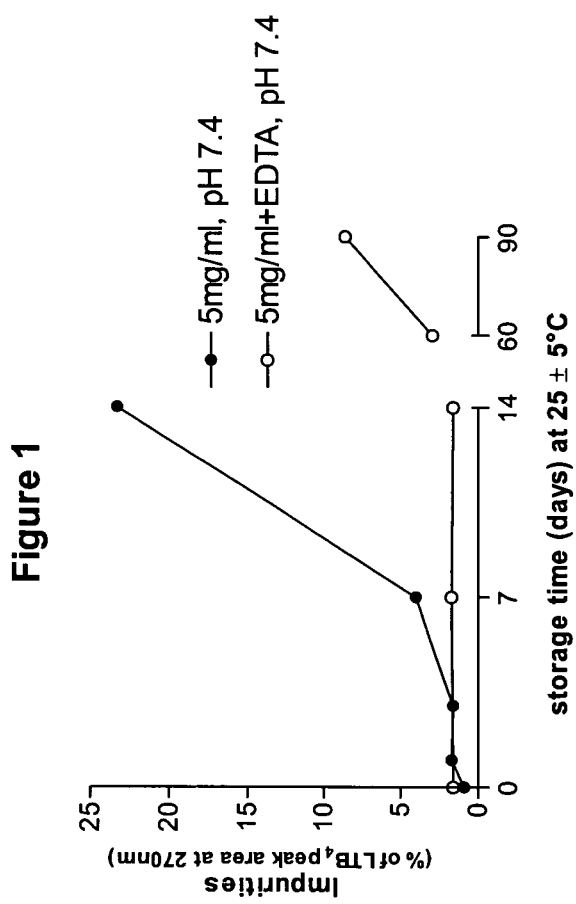
FIG. 1 illustrates that the chelating agent EDTA enhances the stability of an aqueous solution of $LTB_4$ Na salt at pH 7.4.

The stability of aqueous solutions of $LTB_4$ was tested under various experimental conditions. It was found that 1) the stability of $LTB_4$ solutions was dramatically increased at alkaline pH; and 2) chelating agents such as EDTA promote the stability of $LTB_4$ solutions. The positive effect of alkaline pH on $LTB_4$ solution stability was observed using either a phosphate buffer or a glycine buffer; the positive effect of alkaline pH on $LTB_4$ solution stability was observed at all concentrations of the drug tested (17.5 µg/ml to 17.5 mg/ml) and at all temperature tested (4° C. and 40° C.).

When referring to "increased shelf-life" in the context of the present invention, it is intended to mean an extension of the stability of $LTB_4$ agents in the formulations or compositions of the present invention compared to formulations or compositions of $LTB_4$ agents not comprising pH as described above and/or chelating agents as described above. The time period of stability of $LTB_4$ agents in the formulations or compositions of the present invention compared to formulations or compositions of $LTB_4$ agents not comprising pH as described above and/or chelating agents as described above is, depending on temperature, pollution, and concentration of the $LTB_4$ agents, preferably increased by at least a week, such as at least two, three or four weeks, more preferably at least two, three, or four months, especially at least six, nine, or twelve months, such as at least 24 or 48 months.

When referring to the time period of stability of $LTB_4$ agents in formulations or compositions, it is intended to mean the time period wherein the level of impurities is less than 10%, preferably less than 6%, most preferably less than 5%, such as less than 4%, 3%, 2%, or 1%.

The term "impurities" in the context of the present invention is intended to mean the products of the degradation of the $LTB_4$ agent as measured by reverse phase HPLC and UV photometry at 270 nm. Thus, the higher the level of impurities, the lower the stability of the $LTB_4$ agent formulation. In the present description, examples, and figures, the level of impurities is expressed as the percentage of the peak area of the impurities relative to the $LTB_4$ peak area measured by UV photometry at 270 nm. In the Examples and figures pertaining to these, the level of impurities may be expressed as the percentage of the total area under the curve at 270 nm. The applied definition will be clear from the context of the examples.

The term "salts thereof" is intended to mean pharmaceutically acceptable base addition salts obtainable by treating the acid form of a functional group, such as a carboxylic acid, with appropriate bases such as inorganic bases, for example alkaline metal hydroxides; typically sodium or potassium hydroxide; alkaline metal carbonates; typically sodium or potassium carbonate or hydrogencarbonate; alkaline earth metal hydroxides; typically calcium or magnesium hydroxide; alkaline earth metal carbonates; typically calcium or magnesium carbonate or hydrogencarbonate; or ammonia; or organic bases, for example primary, secondary, or tertiary amines, alkaline metal or alkaline earth metal alcoholates, for example sodium methanolate, sodium ethanolate, or potassium ethanolate. Preferred salts of the present invention are base addition salts with sodium or potassium hydroxide. In one embodiment, a preferred salt is the Na salt of $LTB_4$.

The term "esters thereof" is intended to mean pharmaceutically acceptable esters obtainable by treating the acid or acid derivative form of a functional group with any typical esterification agent known to the person skilled in the art. In the context of the present invention, esters of the $LTB_4$ agents defined herein are preferably $C_{1-6}$ alkyl esters, such as methyl ester, ethyl ester, n-propyl ester, i-propyl ester, n-butyl ester, i-butyl ester, s-butyl ester, t-butyl ester, n-pentyl ester, i-pentyl ester, s-pentyl ester, neo-pentyl ester, and n-hexyl ester. Esters of the $LTB_4$ agents defined herein may also be intramolecular esters, i.e. lactones, formed by internal esterification of e.g. the 5-hydroxy group with the carboxylic acid group.

The term "ethers thereof" is intended to mean pharmaceutically acceptable ethers obtainable by treating the alcohol or alcohol derivative form of a functional group with any typical etherification agent known to the person skilled in the art. In the context of the present invention, ethers of the $LTB_4$ agents defined herein are preferably $C_{1-6}$ alkyl ethers, such as methyl ether, ethyl ether, n-propyl ether, i-propyl ether, n-butyl ether, i-butyl ether, s-butyl ether, t-butyl ether, n-pentyl ether, i-pentyl ether, s-pentyl ether, neo-pentyl ether, and n-hexyl ether.

$LTB_4$ Agents

The leukotriene B4 ($LTB_4$) agent of the present invention is either $LTB_4$ or certain structurally related polyunsaturated fatty acids, which mimic their biological activity. The leukotriene B4 ($LTB_4$) agent of the present invention and its structurally related polyunsaturated fatty acids are either natural substances or analogs of such natural substances. All of the $LTB_4$ agents can be obtained by chemical synthesis by methods described in the literature and most are commercially available. Alternatively, the $LTB_4$ agents can be purified forms of the natural substance. In one embodiment, $LTB_4$ itself is a purified form of naturally occurring $LTB_4$.

As used herein, the term "$LTB_4$ agent" includes any a salt thereof, an ester thereof, or an ether thereof and means one or more of the following polyunsaturated fatty acids, which in addition to $LTB_4$ itself, are analogs of $LTB_4$, or precursors or metabolites of $LTB_4$ or $LTB_4$ analogs: $LTB_4$, 14,15-dihydro-$LTB_4$, 17,18-dehydro-$LTB_4$, 19-hydroxy-$LTB_4$, 20-hydroxy-$LTB_4$ and their 5(R)-hydroxy, 5(S)hydroperoxy, 5(R)-hydroperoxy and 5-deoxy analogs; $LTA_4$; 14,15-dihydro-$LTA_4$, 17,18-dehydro-$LTA_4$; 14,15-dihydro-$LTA_4$ methyl ester, $LTA_4$ methyl ester, 5(S)-hydroxy-6,8,11,14(E,Z,Z,Z)-eicosatetraenoic acid ("5-HETE"), 14,15-dihydro-5-HETE, 17,18-dehydro-5-HETE, and their 5(R)-hydroxy, 5(S)-hydroperoxy, and 5(R)-hydroperoxy analogs.

The term $LTB_4$ agent also includes other derivatives of polyunsaturated fatty acids: leukotrienes C4 and D4 and their 14,15-dihydro or 17,18-dehydro analogs; N-acyl or N-alkyl derivatives of leukotrienes C4 and D4 and their 14,15-dihydro or 17,18-dehydro analogs; all isomeric 5,12-dihydroxy-6,8,10,14-eicosatetraenoic acids and 5-hydroxy-6,8,11,14-eicosatetraenoic acids.

The term $LTB_4$ also includes variants which are non-covalently modified fatty acids such as the sodium or the potassium salts of the $LTB_4$ agents.

The term $LTB_4$ agent also includes variants where a modification is introduced into the molecule by reacting targeted functional groups of the fatty acid with an organic derivatizing agent that is capable of reacting with the selected functional group (yielding for example, ester and ether derivatives of $LTB_4$ agent) or to cause intramolecular rearrangement (such as the formation of lactones with hydroxylated fatty acids). The resulting compounds may have altered biological activity and/or bioavailability. Thus, the covalently modified fatty acid can be a pro-drug with reduced biological activity which upon in vivo administration is slowly transformed into a more active molecule (underivatized $LTB_4$ agent). Variants may also be metabolically stable and biologically active analogs of $LTB_4$ agents altered in a way that will result in retarded disposition of the compound (decreased metabolism and/or elimination). Variants with modifications at the omega end (such as 20,20,20-trifluoromethyl-$LTB_4$) show increased resistance to omega-oxidation (a catabolic process of unsaturated fatty acids); other variants with modification at the omega end at the level of carbons 13 to 20 (such as 19-methyl-$LTB_4$ or 19,19-dimethyl-$LTB_4$ or 19-fluoro-$LTB_4$ or 19,19- difluoro-$LTB_4$ or 18,20-difluro-$LTB_4$ or 20-fluoro-$LTB_4$) may show increased resistance to omega-oxidation and variants with modifications at the carboxylic end, at the level of carbon 1, 2, 3 or 4 (for example, 3-thio-$LTB_4$, 3-hydroxy-$LTB_4$, 3-methyl-$LTB_4$ or 3,3-dimethyl-$LTB_4$ or 3-fluoro-$LTB_4$ or 3,3-difluoro-$LTB_4$ or 2,3-difluoro-$LTB_4$, $LTB_4$ methylsulfonylamide, $LTB_4$ methylamide, 1-tetrazole $LTB_4$), may show increased metabolic resistance to beta-oxidation and/or to elimination (such as uptake by probenecide-sensitive organic acid transporter). Other variants with modification(s) at carbon 12, such as 12(R)-methyl-$LTB_4$, may show increased resistance to reduction of the 11,12 double bond (a metabolic pathway of $LTB_4$). Other variants are analogs of $LTB_4$ agents with structural changes, such as changes in chain length (chain length increased or decreased by 1, 2, 3, or 4 carbons), addition of double bond(s), saturation of double bond(s), changes in double bond(s) geometry (cis to trans or vice versa), change of double bond(s) for triple bond(s), change in the configuration of one or several functional group(s) (R to S or S to R), or where one or several functional group(s) or substituent(s) are either removed, added or changed for other functional groups or substituents (including but not limited to hydroperoxyl, carbonyl, sulfhydryl, sulfoxide, sulfone, cysteinyl, glutathionyl, cysteinyl-glycine, methyl, isopropyl, benzyl, chloro, fluoro), or where the positions of one or several functional groups and/or one or several double bonds has been moved by one, two or three carbons relative to the omega end. The $LTB_4$ agent may be a variant carrying one or several of the above mentioned structural modifications.

The term $LTB_4$ agent formulation also includes formulations of compounds which might contain a mixture of two or several $LTB_4$ agents or an $LTB_4$ agent and one or several equally or less active isomer(s) of the $LTB_4$ agent (positional, geometrical or optical isomers).

Infections

The infections which may be treated with the $LTB_4$ agent, in accordance with the invention, are infections caused by human and/or animal microbial pathogens. Furthermore, prevention or prophylaxis of infections and stimulation of neutrophil function with the $LTB_4$ formulations or compositions of the invention are contemplated by the inventors.

The expression "human and/or animal microbial pathogens" is intended to include, without limitation, DNA and RNA viruses in general and Retroviridae, bacteria, fungi and parasites.

Dose Ranges

The therapeutically effective amount of the $LTB_4$ agent to be administered will vary with the particular $LTB_4$ agent used, the type or mode of administration, the concurrent use of other active compounds, host age and size, type, severity and spread of infection, response of individual patients, and the like. In the case of $LTB_4$, it may be administered in sufficient doses to obtain an effective peak or steady-state concentration of about 0.1 nM to 10 µM, preferably 0.1 nM to 1000 nM, more preferably of about 0.25 nM to 2.5 µM, such as 0.25 nM to 25 nM. An effective dose amount of the $LTB_4$ agent may be determined by the clinician after a consideration of all the above-mentioned criteria. In the case of $LTB_4$ agents other than $LTB_4$ which have a different biological activity, the effective peak or steady-state concentration required may be different, for instance up to 25 µM, such as up to 10 µM. The dosage amount of agent necessary to obtain the desired concentrations in blood can be determined by pharmacokinetic studies, as described in Marleau et al., J. Immunol. 150: 206, 1993, and Marleau et al, Br. J. Pharmacol. 112: 654, 1994.

pH

The expression "alkaline pH" is intended to include an alkaline pH between 7.1 and 14 which is effective at stabilizing the $LTB_4$ agent in an aqueous or organic solutions or in solid or freeze-dried formulation of the present invention. Preferred alkaline pH ranges are between 8.2 and 14, especially between 8.5 and 12.5, such as between 8.5 and 11.5, most preferably between 9.5 and 11.5, such as about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, or 11.5. In another preferred embodiment, the preferred alkaline pH ranges between 8.5 and 9.5, between 9.0 and 10.0, between 9.5 and 10.5, or between 10.0 and 11.5. In one embodiment, a preferred pH range is between 9.5 and 10.5.

The expression "alkaline reacting carrier" is intended to include an otherwise inert, pharmaceutically acceptable substance (or substances), which creates an alkaline "micro-pH" between 8.2 and 14, especially between 8.5 and 12.5, such as between 8.5 and 11.5, most preferably between 9.5 and 11.5, such as about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, or 11.5. around each $LTB_4$ particle, in the case of the stabilized $LTB_4$ formulation being in a freeze-dried, crystalline, or solid amorphous form, when water is adsorbed to the particles of the mixture or when water is added in small amounts to the mixture. In another preferred embodiment, the alkaline "micro-pH" ranges between 8.0 and 9.0, between 8.5 and 9.5, between 9.0 and 10.0, between 9.5 and 10.5, or between 10.0 and 11.5. Such substances creating said "micro-pH" can be chosen among, but are not restricted to substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances, such as $Al_2O_3 \cdot 6MgO \cdot CO_2 \cdot 12H_2O$, $(Mg_6Al_2(OH)_{16} CO_3 \cdot 4H_2O)$, $MgO \cdot Al_2O_3 \cdot 2SiO_2 \cdot nH_2O$ or similar compounds; organic pH-buffering substances such as trihydroxymethylaminomethane or other similar, pharmaceutically acceptable pH-buffering substances.

Pharmaceutically Acceptable Carriers

The expression "pharmaceutically acceptable carrier" is intended to include any carrier, such as any aqueous carrier, suitable for physiological and pharmaceutical usage. Such carrier is selected from the group consisting of water, buffered salt solutions, such as phosphate buffered saline (PBS), or sodium chloride solutions buffered with agents such as Tris, glycine or other amino acids, in particular basic amino acids, aqueous solution containing alcohol, such as ethanol, propylenglycol, propanediol, glycerol, or mannitol, as well as sugar solutions, such as glucose or lactose solutions, or a mixture of the various carriers mentioned. Furthermore, the expression "pharmaceutically acceptable carrier" may include inert diluents or fillers, such as sucrose, sorbitol, sugar, mannitol, microcrystalline cellulose, starches including potato starch, calcium carbonate, sodium chloride, lactose, calcium phosphate, calcium sulfate or sodium phosphate; granulating and disintegrating agents, for example, cellulose derivatives including microcrystalline cellulose, starches including potato starch, croscarmellose sodium, alginates or alginic acid; binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone or polyethylene glycol; and lubricating agents, including glidants and antiadhesives, for example, magnesium stearate, zinc stearate, stearic acid, silicas, hydrogenated vegetable oils or talc.

In a particular embodiment of the invention, the expression "pharmaceutically acceptable carrier" only includes non-toxic substances. In a preferred embodiment of the invention, the expression "pharmaceutically acceptable carrier" does not include acetonitrile.

The term "toxic" is used herein in the meaning that is well-known to the person skilled in the art, more particularly, in the context of the formulations of the present invention, a toxic substance is a substance that in the amount present in the formulations of the invention can impair the functioning of, or cause structural damage to a cell or organism. Hence, a "non-toxic substance" does not include acetonitrile.

In a particularly preferred embodiment of the present invention, the formulation comprises only non-toxic substances.

A formulation according to the present invention may comprise less than 25% (vol/vol) acetonitrile, preferably less than 15%, even more preferably less than 5%, most preferably less than 1% (vol/vol).

Any suitable type or mode of administration may be employed for providing a mammal, especially a human with an effective dosage of a $LTB_4$ agent formulation of the present invention. For example, oral, parenteral, intraduodenal, intrajejunal and topical may be employed. Dosage forms include tablets, capsules, powders, solutions, dispersions, suspensions, creams, ointments and aerosols.

For parenteral, for example, subcutaneous or intravenous, or topical administration, the formulation of the present invention is converted into a solution, gel or emulsion, if desired, using the pharmaceutical substances customary for this purpose, such as solubilizers, thickening agents, emulsifiers, agents for tonicity, preservatives or other auxiliaries.

The topical vehicles used in pharmacy are aqueous solutions which are, for example, buffer systems or isotonic or hypertonic mixtures of water and solvents which are miscible with water, such as, for example, alcohols or aryl alcohols, oils, polyalkylene glycols, ethylcellulose, hydroxypropylcellulose carboxymethylcellulose, polyvinylpyrrolidone or copolymers of ethyleneoxide and propyleneoxide (pluronic) isopropylmyristate. Examples of suitable buffer substances are sodium hydroxide and amino acids such as glycine, arginine, histidine and lysine, sodium phosphate, sodium acetate or gluconate buffer. The topical administration form can also contain nontoxic auxiliaries such as, for example, polyethylene glycols, and antibacterial compounds.

Continuous release formulations are also contemplated within the scope of the present invention. Such formulations are of considerable variety, as will be understood by those skilled in the art. Exemplary continuous release substances include organic solvents or biodegradable, biocompatible polymers, including, for example, emulsions, gels, microspheres and hydrogels. Preferred continuous release formulations for use in conjunction with the present invention is the microcapsule or microsphere and micelles. Microcapsules/spheres are essentially small particles of active compounds embedded in a suitable polymer to form spheres ranging in diameter from about 40-500 μm (preferably less than 150 μm) and are easily administered by injection when suspended in a suitable liquid vehicle.

The $LTB_4$ agent can be formulated as a sterile pharmaceutical composition for therapeutic use which is suitable for any topical or systemic mode of administration. The product may be in a solvent-free form (for example a freeze-dried solution containing mannitol) and ready to be reconstituted for use by the addition of a suitable carrier or diluent. Alternatively, the product may be in the form of solution which may be aqueous or organic and ready to be administered or ready to be modified by the addition of a suitable diluent.

For modification of the product in the form of solution in accordance with the present invention one may employ a sterile diluent, which may contain materials generally recognized for approximating physiological conditions. In this manner, the sterile diluent may contain salts and/or buffering agents to achieve a physiologically acceptable tonicity and pH, such as sodium chloride, phosphate and/or other substances which are physiologically acceptable and/or safe for use.

When used as an aqueous solution, the pharmaceutical composition will for the most part contain many of the same substances described above for the reconstitution of a solvent-free product. When used in solution in an organic solvent, a small volume of the solution containing the fatty acid ($LTB_4$ agent) will be diluted with an aqueous solution that will contain many of the same substances described above for the reconstitution of a solvent-free product. The pharmaceutical composition, for the most part, will thus contain many of the same substances described above for the reconstitution of a solvent-free product.

The $LTB_4$ agent may be used in combination with other agents including, but not limited to, antimicrobial agents, anti-cancer agents, immunosuppressive agents, immunostimulatory agents, anti-inflammatory agents, cytokines, growth factors (such as G-CSF, M-CSF, and GM-CSF), retinoids and compounds that may reduce uptake, elimination or metabolism of the $LTB_4$ agent such as probenecide, dipyridamole or clofibrate.

Where the subject $LTB_4$ agent is to be administered to a host as an anti-infectious agent, the agent may be administered, for example, orally, intraarterially, intravenously, intraperitoneally, subcutaneously, intranasally, intramuscularly, by injection, by inhalation, or the like.

Dosage Forms with Enteric Coating

It has been shown in a rat model (Example 11) that intraduodenal administration of the $LTB_4$ agents herein provides a desirable pharmacokinetic profile. Thus, in a preferred embodiment, the formulations of the present invention may be in an oral dosage form with an enteric coating. From what is said about the stability properties of the $LTB_4$ agents listed above, it is obvious that it is advantageous that an oral dosage form of the said $LTB_4$ agents must be protected from contact with the acid reacting gastric juice in order to reach the small intestine without degradation.

The enteric coated preparations are resistant to dissolution in acid media and dissolve rapidly in neutral to alkaline media. The enteric coated dosage form is preferably characterized in the following way. Cores containing the $LTB_4$ agent mixed with alkaline reacting compounds or a salt of the $LTB_4$ agent optionally mixed with an alkaline reacting compound are coated with two or more layers, in which the first layer/layers is/are soluble in water or rapidly disintegrating in water and consist(s) of non-acidic, otherwise inert pharmaceutically acceptable substances. This/these first layer/layers separates/separate the alkaline reacting core material from the outer layer, which is an enteric coating. The final, enteric coated dosage form is treated in a suitable way to reduce the water content to a very low level in order to obtain a good stability of the dosage form during long-term storage.

Cores

The $LTB_4$ agent is mixed with inert, preferably water soluble, conventional pharmaceutical constituents to obtain the preferred concentration of the active compound in the final mixture and with an alkaline reacting, otherwise inert, pharmaceutically acceptable substance (or substances), which creates a "micro-pH" as defined above, when water is adsorbed to the particles of the mixture or when water is added in small amounts to the mixture. Such substances can be chosen among substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances such as $Al_2O_3.6MgOCO_2.12H_2O$, $(Mg_6Al_2(OH)_{16}CO_3.4H_2O)$, $MgO.Al_2O_3.2SiO_2.nH_2O$, wherein n not is an integer and less than 2 or similar compounds; organic pH-buffering substances such as trishydroxymethylaminomethane or other similar, pharmaceutically acceptable pH-buffering substances.

The powder mixture is then formulated into small beads i.e. pellets or tablets, by conventional pharmaceutical procedures. The pellets or tablets are used as cores for further processing.

Separating Layer

The alkaline reacting cores containing an $LTB_4$ agent must be separated from the enteric coating polymer(s) containing free carboxyl groups, which otherwise causes degradation of the $LTB_4$ agent during the coating process or during storage. The subcoating layer, (the separating layer), also serves as a pH-buffering zone in which hydrogen ions diffusing from the outside in towards the alkaline core can react with hydroxyl ions diffusing from the alkaline core towards the surface of the coated particles. The pH-buffering properties of the separating layer can be further strengthened by introducing in the layer substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgOCO_2.12H_2O$, $(Mg_6Al_2(OH)_{16}CO_3,4H_2O)$, $MgO.Al_2O_3.2SiO_2.nH_2O$, wherein n not is an integer and less than 2 or similar compounds; or other pharmaceutically acceptable pH-buffering substances such as, for instance the sodium, potassium, calcium, magnesium and aluminium salts of phosphoric, citric or other suitable, weak, inorganic or organic acids.

The separating layer consists of one or more water soluble inert layers, optionally containing pH-buffering substances.

The separating layer(s) can be applied to the cores—pellets or tablets—by conventional coating procedures in a suitable coating pan or in a fluidized bed apparatus using water and/or conventional organic solvents for the coating solution. The material for the separating layer is chosen among the pharmaceutically acceptable, water soluble, inert compounds or polymers used for film-coating applications such as, for instance sugar, polyethylene glycol, polyvinylpyrollidone, polyvinyl alcohol, hydroxypropyl cellulose, hydroxymethyl cellulose or hydroxypropyl methylcellulose. The thickness of the separating layer is not less than 2 μm, for small spherical pellets preferably not less than 4 μm, for tablets preferably not less than 10 μm.

In the case of tablets another method to apply the coating can be performed by the drycoating technique. First a tablet containing the acid labile compound is compressed as described above. Around this tablet another layer is compressed using a suitable tableting machine. The outer, separating layer, consists of pharmaceutically acceptable, in water soluble or in water rapidly disintegrating tablet excipients. The separating layer has a thickness of not less than 1 mm.

Ordinary plasticizers, pigments, titanium dioxide talc and other additives may also be included into the separating layer.

The enteric coating layer is applied on to the sub-coated cores by conventional coating techniques such as, for instance, pan coating or fluidized bed coating using solutions of polymers in water and/or suitable organic solvents or by using latex suspensions of said polymers. As enteric coating polymers can be used, for example, cellulose acetate phthalate, hydroxypropyl methylcellulose phthalate, polyvinyl acetate phthalate, co-polymerized methacrylic acid/methacrylic acid methyl esters such as, for instance, compounds known under the trade name Eudragit$^R$ L 12,5 or Eudragit$^R$ L 100, (Röhm Pharma) or similar compounds used to obtain enteric coatings.

The enteric coating can also be applied using water-based polymer dispersions, e.g. Aquateric (FMC Corporation), Eudragit$^R$ L 100-55 (Röhm Pharma), Coating CE 5142 (BASF). The enteric coating layer can optionally contain a pharmaceutically acceptable plasticizer such as, for instance, cetanol, triacetin, citric acid esters such as, for instance, those known under the trade name Citroflex$^R$ (Pfizer) phthalic acid esters, dibutyl succinate or similar plasticizers.

The amount of plasticizer is usually optimized for each enteric coating polymer(s) and is usually in the range of 1-20% of the enteric coating polymer(s). Dispersants such as talc, colourants and pigments may also be included into the enteric coating layer.

Thus, the enteric coated preparation according to the invention consists of cores containing the $LTB_4$ agent mixed with an alkaline reacting compound or cores containing an alkaline salt of the acid labile compound mixed with an alkaline reacting compound. The cores are coated with a water soluble or in water rapidly disintegrating coating, optionally containing a pH-buffering substance, which separates the alkaline cores from the enteric coating. The sub-coated dosage form is finally coated with an enteric coating rendering the dosage form insoluble in acid media, but rapidly disintegrating/dissolving in neutral to alkaline media such as, for instance the liquids present in the proximal part of the small intestine, the site where dissolution is wanted.

Chelating Agent

The expression "chelating agent" is intended to include metal chelating agents generally known in the art. Chelators for metal ions are generally polyfunctional molecules which have a multiplicity of negatively charged and/or electron-rich ligands which can sequester metal ions with varying affinities. Suitable electron-rich functional groups include carboxylic acid groups, hydroxy groups and amino groups. Arrangement of these groups in aminopolycarboxylic acids, hydroxypolycarboxylic acids, hydroxyaminocarboxylic acids, and the like result in moieties which behave as excellent chelators. These include aminopolycarboxylic acids such as, for example, ethylenediaminetetraacetic acid (EDTA), diethylenetriamine pentaacetic acid (DTPA), nitrilotriacetic acid (NTA), N-2-acetamido-2-iminodiacetic acid (ADA), bis (aminoethyl)glycolether, N,N,N',N'-tetraacetic acid (EGTA), trans-diaminocyclohexane tetraacetic acid (DCTA), glutamic acid, and aspartic acid; and hydroxyaminocarboxylic acids, such as, for example, N-hydroxyethyliminodiacetic acid (HIMDA), N,N-bis-hydroxyethylglycine (bicine) and N-(trishydroxymethylmethyl)glycine (tricine); and N-substituted glycines such as glycylglycine. Other candidate chelators include 2-(2-amino-2-oxoethyl)aminoethane sulfonic acid (BES). All the foregoing also include the salts of carboxyl or other acidic functionalities.

Examples of such salts include salts formed with sodium, potassium, and other weakly bound metal ions; the nature of the salt and the number of charges to be neutralized will depend on the number of carboxyl groups present and the pH at which the stabilizing chelator is supplied.

As is understood in the art, chelating agents have varying strengths with which particular target ions are bound. In general, heavy metal ions are bound more strongly than their similarly charged lower molecular weight counterparts. For example, $Cu^{+2}$ is uniformly chelated more strongly than $Ca^{+2}$, accounting for the ability, in some instances, to use calcium salts of the chelators supplied. In order to assess relative strength, the stability constant with respect to copper ion at the pH of the formulation is used herein as an arbitrary standard for comparison of chelators. These stability constants are, of course, pH dependent, readily available in the literature, and can be found for example, in Perrin, D. D., et al., "Buffers for pH and Metal Ion Control" Chapman & Hall, London, N.Y., (1974), and, in particular, in International Union of Pure & Applied Chemistry: "Stability Constants", suppl 1 (1971) Alden press, Oxford. Using the values for stability of the $Cu^{+2}$ complexes found in these references as a measure of the strength of the chelator, one can set classifications of chelator strength. The "log beta" values are used, these are the negative logarithms of the dissociation constant for the complex. The higher the value of log-beta, therefore, the stronger the association between the copper ion and the chelating moiety. Of course, the pH at which determination is made is significant, since the various carboxylic acid groups contained in the chelator bind more strongly to the sequestered ion when they are negatively charged.

Particularly useful in the invention are chelators with log-beta values for copper ion (as determined at the pH of the proposed formulation) of about 7 or more; more preferred are those with values of 10 or more; and most preferred are those with log-beta values at the pH of use of 15 or more. Thus, for example, tricine, bicine, ADA and HIMDA are preferred, as these are fairly strong; even more preferred are NTA, DTPA, and EDTA. Among the most preferred chelators for use in the invention are EDTA and DTPA.

A large number of chelating agents is known in the art, and a candidate chelator can readily be evaluated by determination of its log-beta value with respect to copper ion at the intended pH of use and, provided it has pharmaceutically acceptable properties which permit its use in compositions to be administered to the patients, can be evaluated conveniently for use in the invention method and in the invention compositions.

Solubilities in water should also be considered, though the various chelators may be present in different amounts, depending on the nature of the remainder of the formulation. While the chelating agent is present in stabilizing amounts, the percent chelating agent total weight can be of from about 0.001% to about 1.0% percent (weight/weight) of the overall formulation. Preferably, the percent chelating agent total weight is present in amounts of from about 0.01% to about 0.1% percent (weight/weight). These values refer to final reconstituted product for pharmaceutical indications. If the formulation is lyophilized, the percent chelating agent in the dry cake may be as high as about 10% to about 40%. Therefore, in dry form the chelating agent can be present in amounts of about 0.01% to about 40% total weight, preferably about 1.0% to about 30%. As one of skill in the art would recognize, the percentage of the chelating agent in the formulation varies depending upon the particular bulking agent used to formulate the active compound. Clearly, the higher the levels of problematic metal ions present in the bulking agent or otherwise in the composition, the higher the levels of chelator required. It is a simple matter, using the techniques described hereinbelow, to determine optimal concentrations of the chelating agent.

The present invention will be more readily understood by referring to the following examples which are given to illustrate the invention rather than to limit its scope.

EXAMPLE 1

Materials and Methods $LTB_4$ (acid form) was obtained from Cascade Biochem (U.K.) in solution in ethanol/water, 95/5. The purity level of this starting material was about 98.5% (+0.3%) as assessed by reverse phase HPLC. The ethanolic $LTB_4$ solution was neutralized with an equivalent of sodium hydroxide to obtain $LTB_4$ sodium (Na) salt. The ethanolic solution of $LTB_4$ Na salt was evaporated to dryness under reduced pressure using a rotoevaporator and a water bath (30° C.), until an oily residue is obtained. The residue was redissolved in Dulbeccos' phosphate buffered saline (DPBS) at pH 7.4 containing or not, 0.01% ethylenediaminetetraacetic acid (EDTA) to obtain a final concentration of 5 mg $LTB_4$/ml. Solutions were dispensed in 2 ml type I borosilicate glass vials which were then sealed under argon using Teflon-lined rubber stoppers and aluminium caps. The samples were stored in the dark at 25±5° C. until analysis at the indicated time points. Analysis of $LTB_4$ solutions was carried out by reverse phase HPLC using a C18, 5μ particle, 4.7X250 mm column (Nucleosil) and methanol/acetonitrile gradient elution; detection of $LTB_4$ and impurities was performed on line using an HPLC UV spectrophotometer at 270 nm.

Results

As shown in FIG. 1, the aqueous $LTB_4$ Na salt solutions at 5 mg/ml containing no EDTA already showed an increased level of impurities after 7 days of storage at 25° C., and the impurity level reached 23.3% of $LTB_4$ peak area after 14 days of storage. In contrast, the $LTB_4$ Na salt solutions at 5 mg/ml containing 0.01% EDTA showed no increase of degradation up to 14 days of storage, and had impurity levels of 2.9% and 8.6% after 60 and 90 days of storage at 25° C., respectively. These data clearly demonstrate that EDTA dramatically slows down the degradation of aqueous solutions of $LTB_4$ Na salt.

EXAMPLE 2

Materials and Methods

A solution of $LTB_4$ (acid form) at the concentration of 12 mg/ml in ethanol/water, 95/5 (from Cascade Biochem, U.K.), was neutralized with an equivalent of sodium hydroxide to generate the Na salt. This starting material used in experiments described in Examples 2 through 7, had a purity level of 96.8% (±0.3%) as assessed by reverse phase HPLC. The ethanolic solution of $LTB_4$ Na salt was evaporated (see Example 1) until an oily residue is obtained. The residue was then redissolved in a phosphate buffered sodium chloride solution (saline) (30 mM sodium phosphate, pH 7.5) containing 0.01% EDTA in order to obtain an isotonic solution of $LTB_4$ Na salt at 25 mg/ml. $LTB_4$ Na salt solution at 0.1 mg/ml was obtained by dilution of the 25 mg/ml solution with an isotonic 30 mM sodium phosphate buffered saline, pH 7.5 containing 0.01% EDTA. Aliquots of the solutions were dispensed in 2 ml type I glass vials as described in Example 1, and stored under air, in the dark, at 40±5° C. $LTB_4$ and impurities were analyzed at the indicated times by reverse phase HPLC using UV detection at 270 nm.

Results

Figure 2:
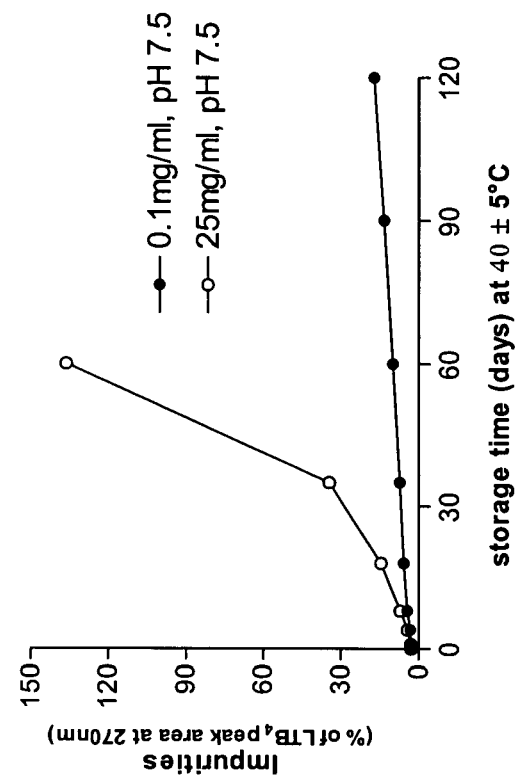
FIG. 2 illustrates the effect of $LTB_4$ concentration on the stability of aqueous solutions of $LTB_4$ Na salt.

FIG. 2 shows the results of a forced degradation study (40° C.) of aqueous isotonic pH 7.5 solutions of LTB$_4$ Na salt at concentrations of 0.1 and 25 mg/ml. The data clearly demonstrate that the 25 mg/ml solution of LTB$_4$ Na salt is much less stable than the LTB$_4$ Na salt solution at 0.1 mg/ml, indicating an inverse relationship between stability and concentration in LTB$_4$ Na salt solutions. The stability of an LTB$_4$ Na salt solution at 0.01 mg/ml was similar to that of the solution at 0.1 mg/ml (data not shown).

EXAMPLE 3

Materials and Methods

Aqueous isotonic LTB$_4$ Na salt solutions at the concentration of 1.75 mg/ml in phosphate/glycine buffered saline (3 mM sodium phosphate and 10 mM glycine buffer, pH 7.5, 8.5, 9.5 and 10.5) containing 0.01% EDTA were obtained by dilution of a 25 mg/ml solution of LTB$_4$ Na salt (see Example 2) with the appropriate phosphate/glycine buffered saline containing 0.01% EDTA. Solutions were dispensed in 2 ml vials for storage under air, in the dark at 4±4° C. and 20±5° C. for 9 months prior to reverse phase HPLC analysis of LTB$_4$ and impurities as described in Example 1.

Results

Figure 3:
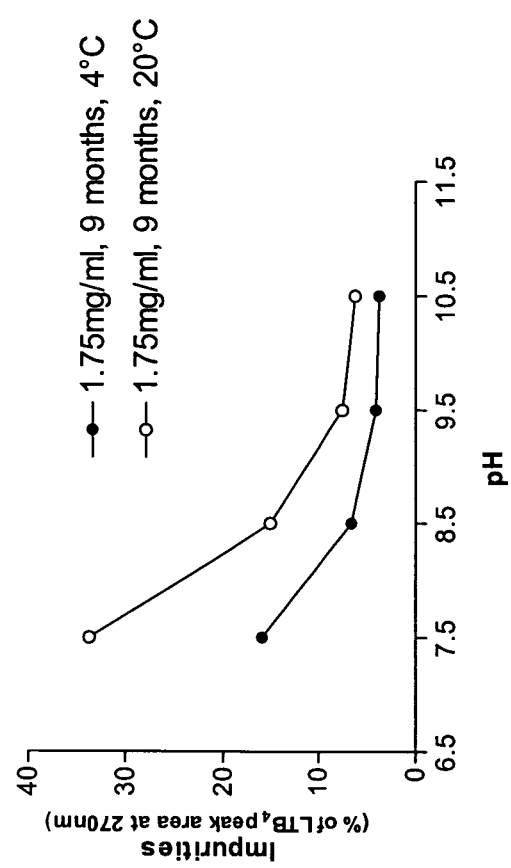
FIG. 3 illustrates the effect of pH (phosphate/glycine buffer) on the stability of an aqueous solution of $LTB_4$ Na salt at 1.75 mg/ml.

FIG. 3 clearly shows that increasing the pH of aqueous isotonic LTB$_4$ Na salt solutions strikingly increases the stability of LTB$_4$ as seen by the reduced levels of impurities detected by HPLC analysis of the samples. This stabilising effect of alkaline pH on LTB$_4$ Na salt solutions was observed at both 4° C. and 20° C., indicating that the stabilizing effect of alkaline pH is not temperature dependent. In forced degradation studies (storage at 40° C.) increasing the pH of LTB$_4$ Na salt solutions also resulted in a dramatic improvement of LTB$_4$ Na salt solution stability (data not shown).

EXAMPLE 4

Materials and Methods

Aqueous isotonic LTB$_4$ Na salt solutions at the concentration of 17.5 μg/ml were obtained by dilution in phosphate buffered saline (3 mM sodium phosphate buffer, pH 7.5, 8.5, 9.5 and 10.5) containing 0.01% EDTA of an LTB$_4$ Na salt solution at 25 mg/ml (Example 2). Solutions of LTB$_4$ Na salt at 17.5 μg/ml of the 4 different pH were dispensed in 2 ml vials for storage under air, in the dark at 4±4° C. or 20±5° C. for 15 months prior to reverse phase HPLC analysis of LTB$_4$ and impurities, as described in Example 1.

Results

Figure 4:
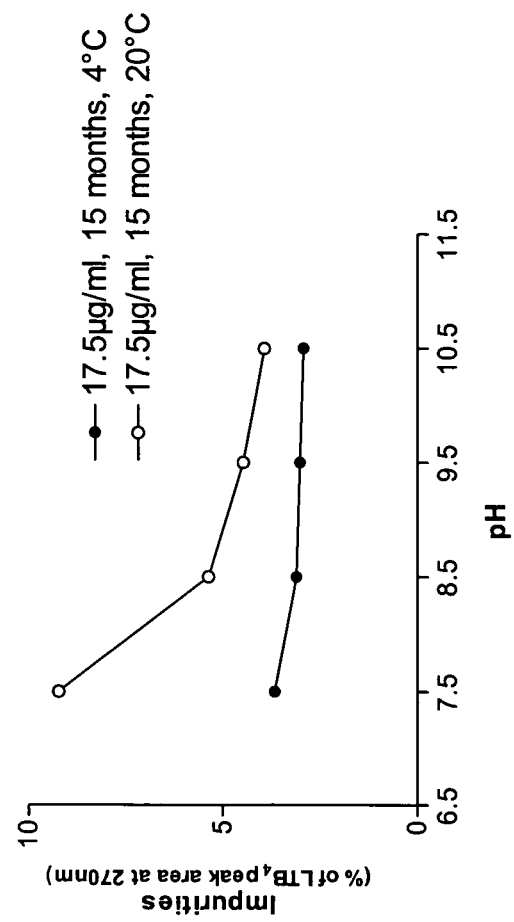
FIG. 4 illustrates the effect of pH (phosphate buffer) on the stability of aqueous solutions of $LTB_4$ Na salt at 17.5 μg/ml.

FIG. 4 clearly shows that increasing the pH of aqueous isotonic LTB$_4$ Na salt solutions at 17.5 μg/ml strikingly increases the stability of LTB$_4$ as seen by the reduced level of impurities detected by HPLC analysis of the samples. This stabilizing effect of alkaline pH on LTB$_4$ Na salt solutions at 17.5 μg/ml was much more evident at 20° C. since at 4° C., the same solutions showed very little degradation of LTB$_4$ after 15 months of storage. These data, together with the data shown in FIG. 3, demonstrate that the stabilizing effect of alkaline pH is clearly observed with LTB$_4$ Na salt solutions at 1.75 mg/ml as well as 17.5 μg/ml, and therefore that the stabilizing effect of alkaline pH occurs over a wide range of concentrations of LTB$_4$.

EXAMPLE 5

Materials and Methods

Aqueous isotonic LTB$_4$ Na salt solutions at the concentration of 35 and 350 μg/ml in phosphate buffered saline (3 mM sodium phosphate buffer, pH 9.5) containing 0.01% EDTA and various concentrations of glycine (from 0.01 mM to 10 mM) were obtained by dilution of a 25 mg/ml solution of LTB$_4$ Na salt (Example 2). Solutions of LTB$_4$ Na salt at 35 and 350 μg/ml at the 4 different glycine concentrations were dispensed in 2 ml vials for storage under air in the dark at 40±5° C. for 5 months prior to reverse phase HPLC analysis of LTB$_4$ and impurities as described in Example 1.

Results

Figure 5:
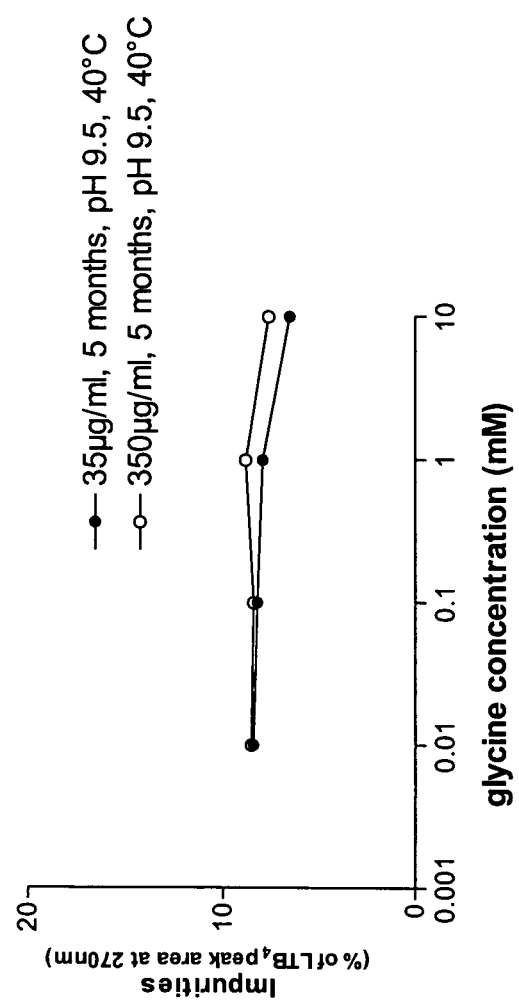
FIG. 5 illustrates the effect of different buffer strengths (phosphate/glycine buffer) on the stability of aqueous solutions of $LTB_4$ Na salt.

In this experiment, a solution of LTB$_4$ Na salt at 35 μg/ml, pH 7.5, containing 10 mM glycine and stored for 5 months at 40° C. showed a level of impurities of 20% (data not shown). FIG. 5 shows that the same LTB$_4$ Na salt solution at 35 μg/ml, but at pH 9.5 was more stable as indicated by the lower level of impurities measured (6.5%), and clearly demonstrates that the concentration of the glycine buffer ranging from 0.01 mM to 10 mM had little impact on the stability of the LTB$_4$ Na salt solutions. A very similar observation was done with solutions of LTB$_4$ Na salt at 350 μg/ml, pH 9.5, stored for 5 months at 40° C., at the same 4 different concentrations of glycine.

EXAMPLE 6

Materials and Methods

Aqueous isotonic LTB$_4$ Na salt solutions at the concentration of 35 μg/ml in phosphate buffered saline (3 mM sodium phosphate buffer, pH 7.5 or 9.5) containing 0.01% EDTA were obtained as described in Example 5. Mannitol was added to all solutions to the final concentration of 4% in order to generate a solid residue (mannitol bread) containing LTB$_4$ Na salt and all components of the excipient upon freeze-drying. Fatty acid free (delipidated) human serum albumine (HSA, Sigma Chemicals, St-Louis, Mo.) was added to some of the solutions to the final concentration of 1 mg/ml prior to final pH adjustment (to 7.5 or 9.5). Solutions were dispensed in 2 ml vials, frozen at −20° C. and freeze-dried. The vials containing the freeze-dried solutions (mannitol breads) were then sealed as described in Example 1 (but under air instead of argon), and stored in the dark at 40±5° C. After 1.5 or 4.5 months, vials were opened and the mannitol breads (containing LTB$_4$) were dissolved using 1 ml of water to regenerate the original LTB$_4$ Na salt solutions at 35 μg/ml. LTB$_4$ and impurities were then analyzed by reverse phase HPLC as described in Example 1.

Results

Figure 6:
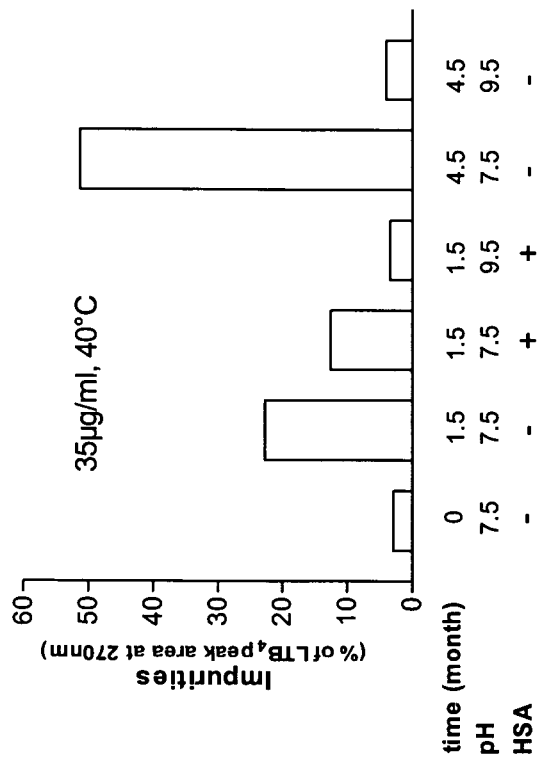
FIG. 6 illustrates that human serum albumine (HSA) or/and alkaline pH (phosphate buffer) enhances the stability of aqueous freeze-dryed solutions (containing mannitol) of $LTB_4$ Na salt.

FIG. 6 shows that a freeze-dried LTB$_4$ Na salt solution at 35 μg/ml, pH 7.5, immediately redissolved in water after freeze-drying (time 0) shows a level of impurities of 2.9%, and that identical freeze-dried samples stored 1.5 and 4.5 months at 40° C. show levels of impurities of 22.7% and 51.3%, respectively. FIG. 6 also shows that addition of HSA to a LTB$_4$ Na salt solution (pH 7.5) prior to freeze-drying results in a nearly 50% decrease in the level of impurities after 1.5 months of storage. FIG. 6 also clearly shows that elevation of pH from 7.5 to 9.5 in LTB$_4$ solutions prior to freeze-drying results in a striking decrease in the level of impurities as observed both after 1.5 months of storage (in the presence of HSA) or after 4.5 months of storage. These data clearly demonstrate that alkaline pH also enhances the stability of LTB$_4$ Na salt in solid form, i.e. after freeze-drying in the presence of mannitol and in the presence or absence of HSA.

EXAMPLE 7

Materials and Methods

The ethanolic solution of $LTB_4$ (acid form) (EtOH/water, 95/5) obtained from the manufacturer (Cascade Biochem, UK) was diluted with EtOH/water, 95/5 to generate ethanolic solutions of $LTB_4$ (acid form) at 9 and 0.9 mg/ml. Ethanolic solutions of the sodium salt of $LTB_4$ at 9 and 0.9 mg/ml were obtained by adding 1.05 equivalent of sodium hydroxide. Solutions of the sodium salt of $LTB_4$ at the concentration of 9 and 0.9 mg/ml in 75/25 EtOH/10 mM glycine in water at pH 10.5 (sodium hydroxide), were obtained by mixing 3 volumes of solutions of the sodium salt of $LTB_4$ at 12 and 1.2 mg/ml in EtOH/water, 95/5 with 1 volume of 40 mM glycine buffer at pH 10.5. Solutions were dispensed in 2 ml vials for storage under air in the dark at −80° C. and 40±5° C. for 17 months prior to reverse phase HPLC analysis of $LTB_4$ and impurities as described in Example 1.

Results

Figure 7:
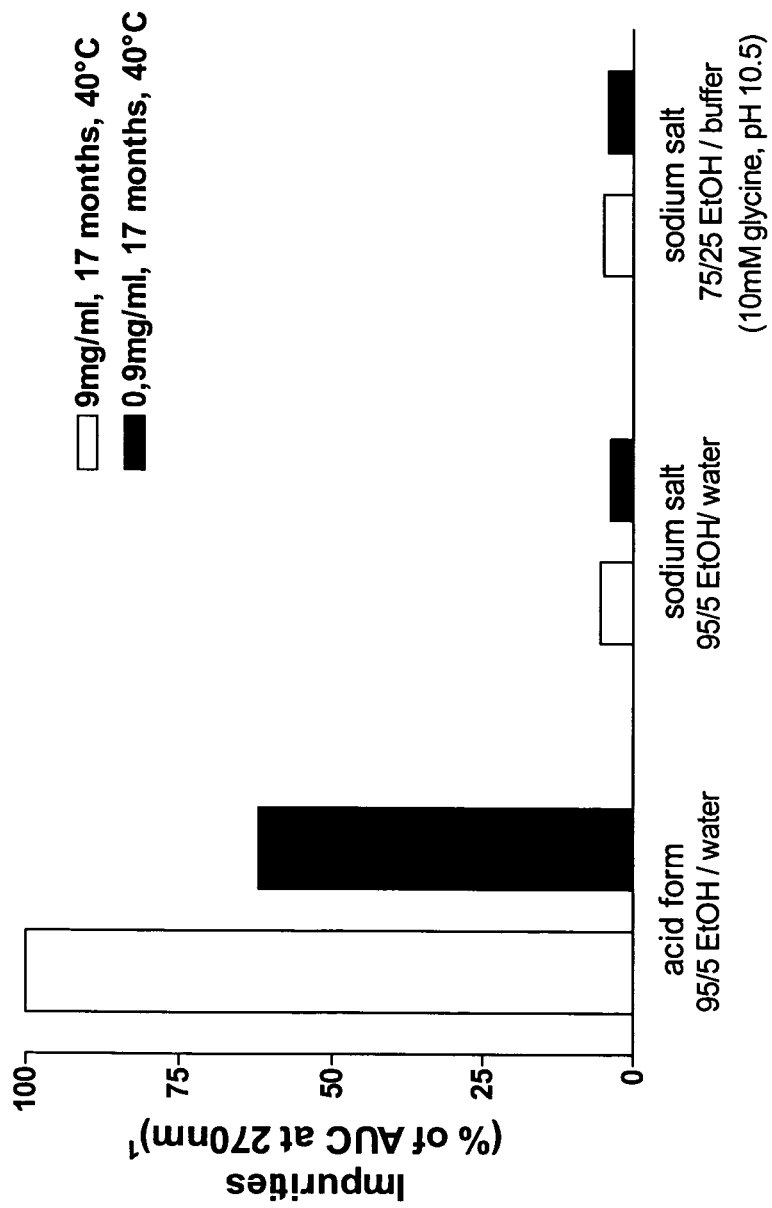
FIG. 7 illustrates that alkaline pH (phosphate/glycine buffer) enhances the stability of ethanolic solutions (95/5, ethanol/water and 75/25, ethanol/buffer, Vol/Vol) of $LTB_4$ (acid form and Na salt).

The results of this forced degradation study of ethanolic solutions of $LTB_4$ (acid form) or $LTB_4$ Na salt at 2 different concentrations are shown in FIG. 7. After 17 months of storage at 40° C., the $LTB_4$ (acid form) ethanolic (EtOH/water, 95/5) solution at 9.0 mg/ml showed complete degradation ($LTB_4$ not detectable) with a level of impurities of 100% of AUC (area under the curve at 270 nm). FIG. 7 clearly shows that when $LTB_4$ was transformed to its sodium salt by addition of 1.05 equivalent of sodium hydroxide, the stability of the resulting ethanolic $LTB_4$ Na salt solution under identical conditions is drastically improved with an impurity level of only 5.4%. Similarly, the forced degradation study of the $LTB_4$ sodium salt solution in 75/25 EtOH 10 mM glycine pH 10.5, demonstrated that under alkaline pH the sodium salt of $LTB_4$ is strikingly more stable (impurity level of 3.8%) than $LTB_4$ in its acid form in EtOH/water, 95/5. The same conclusions can be drawn for solutions of $LTB_4$ (acid form) and $LTB_4$ sodium salt at a 10-fold lower concentration (0.9 mg/ml), with an increased stability of the sodium salt of $LTB_4$ in 95/5 EtOH/water or 75/25 EtOH/10 mM glycine pH 10.5 (impurity levels of 4.9 and 4.3% of AUC, respectively), over the acid form of $LTB_4$ in 95/5 EtOH water (impurity level 62% of AUC). The impurity levels measured in the same 3 ethanolic formulations of $LTB_4$ at 9 and 0.9 mg/ml stored at −80° C. for 17 months varied from 2.8 to 3.7% of AUC (data not shown). Table 1 below displays the pH values measured in the ethanolic formulations of $LTB_4$ stored for 17 months at −80° C. and 40° C. The data clearly demonstrate that enhanced stability do correspond to higher pH of the formulations. Finally, FIG. 7 also shows that, in analogy to the observations made with aqueous solutions of $LTB_4$ Na salt, the more concentrated (9 mg/ml) solution of $LTB_4$ in 95/5 EtOH/water is less stable than the more diluted (0.9 mg/ml) solution of $LTB_4$ in the same experimental conditions.

TABLE 1

Apparent pH[1] in ethanolic formulations of $LTB_4$

| Formulation | −80° C. | +40° C. |
|---|---|---|
| 9 mg/ml, acid form in 95/5 EtOH/water | 7.08[2] | 5.27 |
| 9 mg/ml, sodium salt in 95/5 EtOH/water | 10.15 | 9.68 |
| 9 mg/ml, sodium salt in 75/25 EtOH/buffer[3] | 12.54 | 10.07 |
| 0.9 mg/ml, acid form in 95/5 EtOH/water | 7.25 | 5.26 |
| 0.9 mg/ml, sodium salt in 95/5 EtOH/water | 9.80 | 9.77 |
| 0.9 mg/ml, sodium salt in 75/25 EtOH/buffer[3] | 10.77 | 10.17 |

[1]pH was measured using a Fisher Scientific Accumet microsize miniature pH combination electrode, at room temperature.
[2]pH was measured after 17 months of storage at the indicated temperatures
[3]10 mM glycine/NaOH, pH 10.5

EXAMPLE 8

Materials and Methods $LTB_4$ and analogs were obtained as ethanolic solutions, in acid form. $LTB_4$ was from Cascade Biochem (UK), $LTB_5$ was obtained from Biomol (Plymouth Meeting, Pa., USA) and all other compounds ($LTB_3$, trifluoro-$LTB_4$, 20-hydroxy-$LTB_4$, and 5-HETE) were obtained from Cayman Chemicals (Ann Arbor, Mich., USA). Ethanolic solutions of the sodium salt of the various $LTB_4$ agents ($LTB_4$ and analogs) were obtained by adding 1 equivalent of sodium hydroxide. The ethanolic solutions of the sodium salt of the $LTB_4$ agents were evaporated to dryness under a stream of nitrogen and redissolved at the concentration of ~35 µg/ml in phosphate (30 mM) buffered saline containing 10 mM glycine, 0.01% EDTA, adjusted to pH 7.5 or pH 9.5 with sodium hydroxide. Aliquots of the solutions were taken for immediate analysis (to) and the remaining solutions of $LTB_4$ agent Na salt at 35 µg/ml were dispensed into 2 ml vials for storage under air in the dark at 40±5° C. for six months prior to reverse phase HPLC analysis of the $LTB_4$ agents and impurities as described in example 1.

Results

Figure 8:
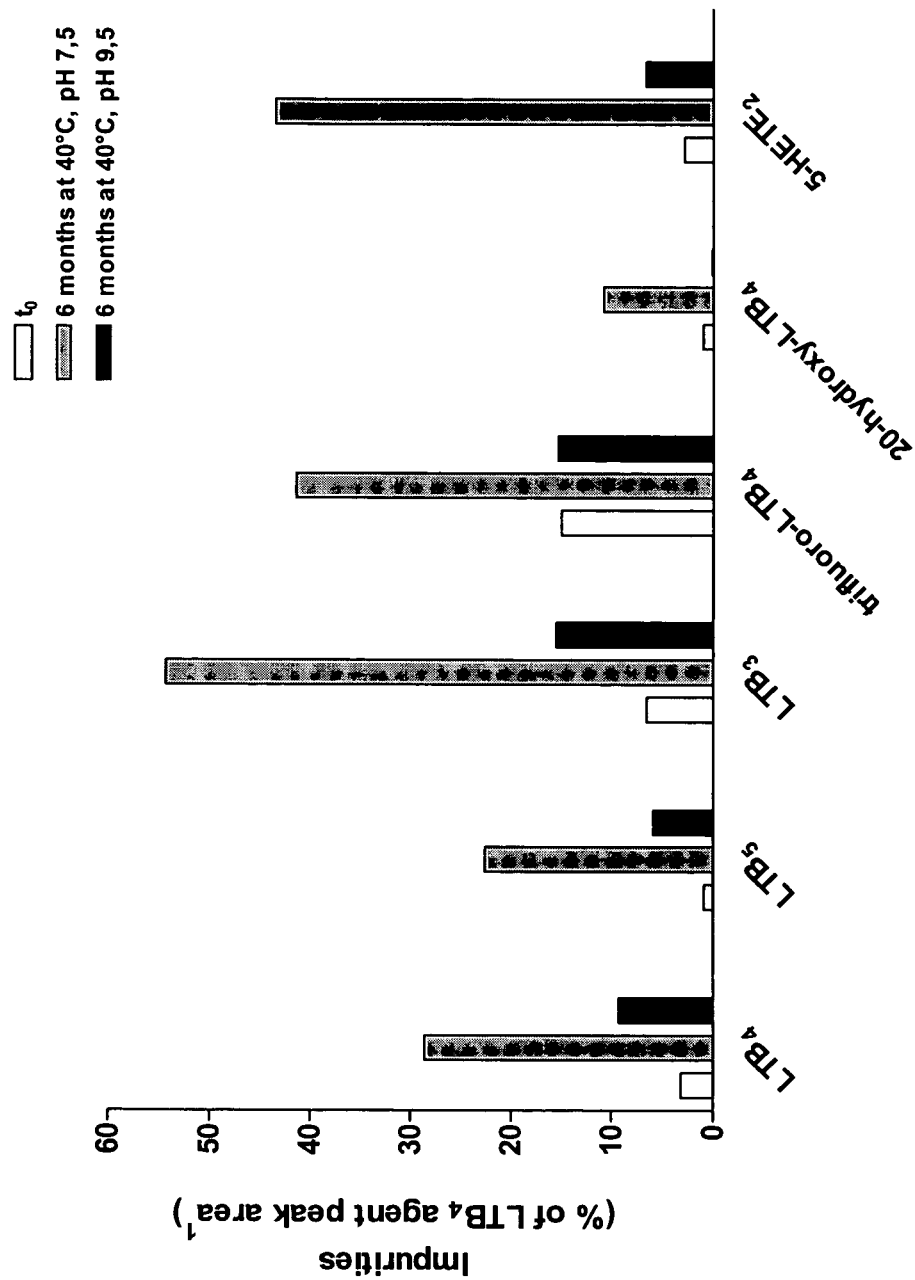
FIG. 8 illustrates that alkaline pH (phosphate/glycine buffer) enhances the stability of various $LTB_4$ agents in solution.

In this experiment, the various solutions of $LTB_4$ agents sodium salt at 35 µg/ml showed an initial (to) impurity level varying from 2 to 15%, as shown in FIG. 8 (empty bars). FIG. 8 shows that the impurity levels in all $LTB_4$ agent solutions stored for six months at 40° C. at pH 7.5 increased significantly (grey bars). FIG. 8 also shows that solutions of the same $LTB_4$ agents stored for six months at 40° C., but at the higher pH of 9.5 are significantly more stable as demonstrated by the lower impurity levels of all solutions (black bars).

EXAMPLE 9

Materials and Methods $LTB_4$ and analogs were obtained as ethanolic solutions, in acid form. Enantio-$LTB_4$ was from Cascade Biochem (UK), and all other compounds (6-trans-$LTB_4$, 12-epi-$LTB_4$ and 6-trans-12-epi-$LTB_4$) were obtained from Cayman Chemicals (Ann Arbor, Mich., USA). Ethanolic solutions of the sodium salt of the various $LTB_4$ agents ($LTB_4$ and analogs) were obtained by adding 1 equivalent of sodium hydroxide. The ethanolic solutions of the sodium salt of the $LTB_4$ agents were evaporated to dryness under a stream of nitrogen and redissolved at the concentration of ~35 µg/ml in phosphate (30 mM) buffered saline containing 10 mM glycine, 0.01% EDTA adjusted to pH 7.5 or pH 9.5 with sodium hydroxide. Aliquots of the solutions were taken for immediate analysis (to) and the remaining solutions of $LTB_4$ agent Na salt at 35 µg/ml were dispensed into 2 ml vials for storage under air in the dark at 40±5° C. for six months prior to reverse phase HPLC analysis of the $LTB_4$ agents and impurities as described in example 1.

Results

Figure 9:
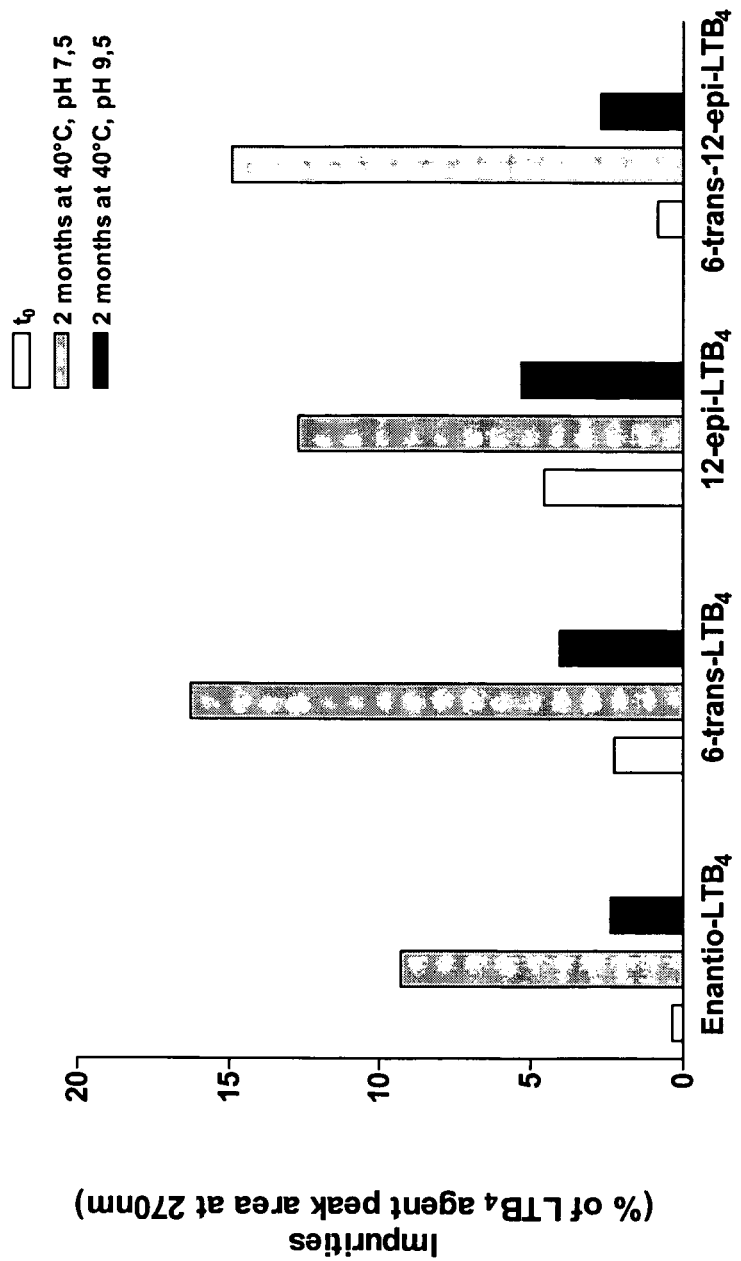
FIG. 9 further illustrates that alkaline pH (phosphate/glycine buffer) enhances the stability of various $LTB_4$ agents in solution.

In this experiment, the various solutions of $LTB_4$ agents sodium salt at 35 µg/ml showed an initial (to) impurity level of 2 to 5%, as shown in FIG. 9 (empty bars). FIG. 9 shows that the impurity levels in all $LTB_4$ agent solutions stored for six months at 40° C. at pH 7.5 increased significantly (grey bars). FIG. 9 also shows that solutions of the same $LTB_4$ agents stored for six months at 40° C., but at the higher pH of 9.5 are significantly more stable as demonstrated by the lower impurity levels of all solutions (black bars).

EXAMPLE 10

Materials and Methods

An ethanolic solution of $LTB_4$ (acid form) obtained from Cascade Biochem (UK) was neutralized by the addition of 1 equivalent of sodium hydroxide to generate $LTB_4$ sodium salt. Aliquots of the ethanolic solution of the sodium salt of $LTB_4$ were dispensed into 2-ml vials (to obtain 2 mg of $LTB_4$ per vial) and the solvent was evaporated to dryness under a stream of nitrogen. The residues in vials were dissolved with 0.9% sodium chloride (NaCl) (vial 1), 0.9% NaCl in 0.1 mN NaOH (vial 2), 0.9% NaCl in 1 mN NaOH (vial 3), 0.9% NaCl in 10 mN NaOH (vial 4), 0.3% NaCl in 0.1N NaOH (vial 5) and in 1N NaOH (vial 6). Aliquots of the solutions were taken for immediate analysis (to) and the remaining solutions of $LTB_4$ sodium salt at 2 mg/ml were stored under air, in the dark at 40±5° C. for five weeks, prior to reverse phase HPLC analysis of $LTB_4$ and impurities as described in example 1.

Results

Figure 10:
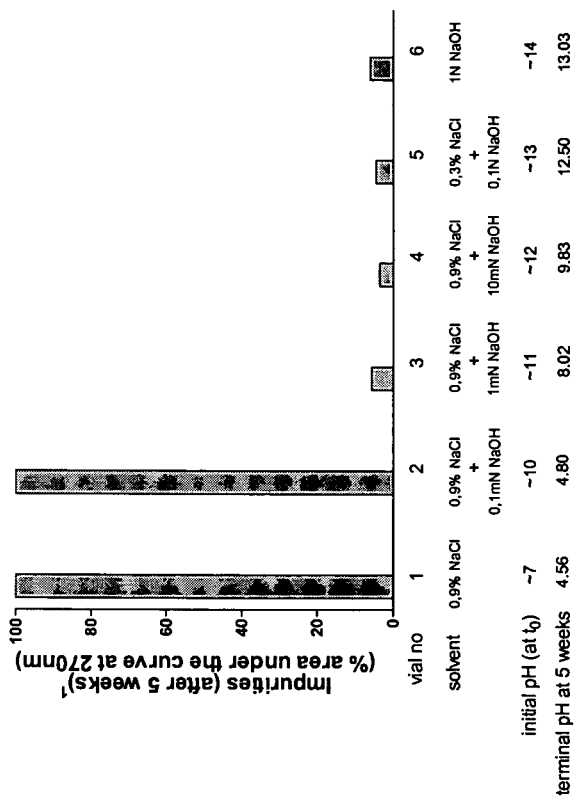
FIG. 10 illustrates that $LTB_4$ is stabilized over a wide range of alkaline pH and that the high pH must be maintained to ensure stability.

The results of this forced degradation study of aqueous solutions of $LTB_4$ sodium salt at increasing concentrations of sodium hydroxide (increasing pH) is shown in FIG. 10. The data obtained demonstrate that $LTB_4$ sodium salt was completely degraded with impurity levels at 100% ($LTB_4$ not detectable) in vials #1 and #2 in which the pH had dropped to values below pH 5 after five weeks of storage at 40° C. In contrast, in vials 3 to 6, in which the final pH (after five weeks) was 8.02, 9.83, 12.50 and 13.03, respectively, the impurity levels were measured at 5.34, 3.46, 4.38 and 5.77 (% of AUC 270 nm), respectively. Initial impurity levels (at to) varied from 2.65 to 3.35%. These data clearly demonstrate that $LTB_4$ sodium salt solutions are strikingly stabilized at alkaline pH, over a very wide range of pH, and in absence of a buffer and a chelating agent.

EXAMPLE 11

In this example, the pharmacokinetics of $LTB_4$ in rats following administration by three distinct routes, intravenous (i.v.), intra-jejunal (i.j.) and sub-cutaneous (s.c.) was investigated.

Three groups of three female Sprague-Dawley rats (weighing ~250 g) were used; animals were fasted for 18 hours, anesthetised with ketamine/xylazine and their jugular veins were canulated to allow for repeated blood sampling. $LTB_4$ was administered at the dose of 50 µg/kg at the dose volume of 4 ml/kg for all routes. Blood samples (0.5 ml/sample) where taken at 0, 0.5, 1, 2, 5, 15, 30, and 60 minutes following $LTB_4$ injection. The blood samples where immediately anticoagulated with EDTA and transferred into an ice-water bath until centrifugation for plasma isolation. Plasma samples were stored at −80° C. until assayed for $LTB_4$ content using a commercial ELISA (Cayman Chemicals, Ann Arbor, Mich., USA). The i.v administration (15 sec. bolus) of $LTB_4$ was done through the tail vein; for i.j. administration, $LTB_4$ was directly injected in the jejunum after opening of the abdominal cavity; s.c. administration was done in the dorsal region.

Figure 11:
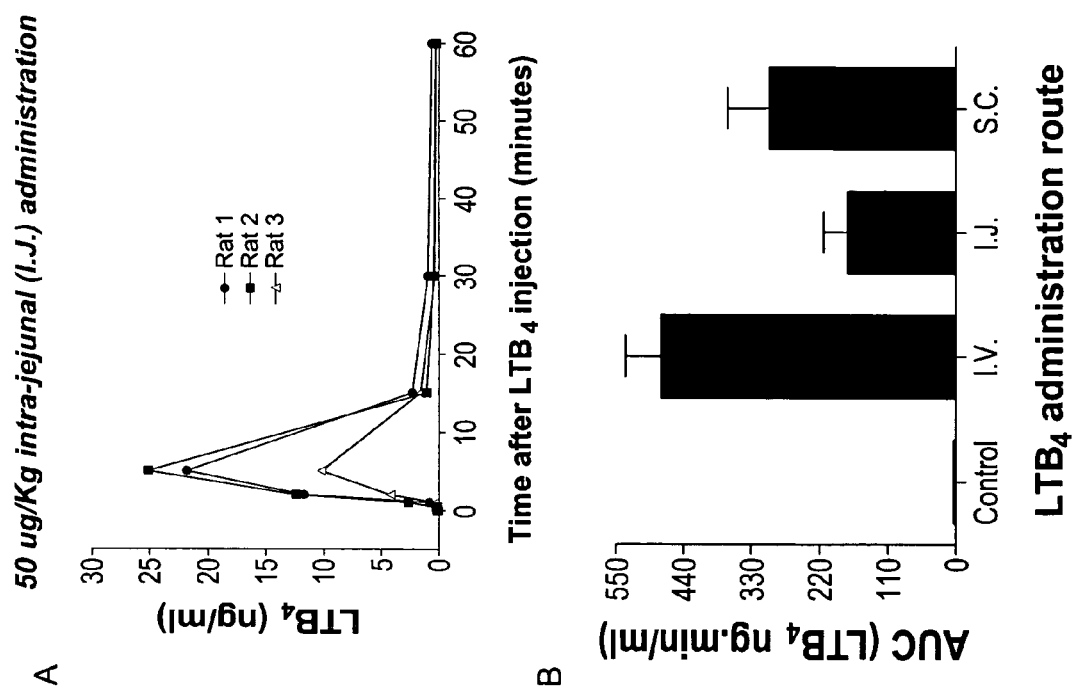
FIG. 11 illustrates the efficient uptake of $LTB_4$ in a rat model by intra-jejunal administration and compares with intravenous and subcutaneous administration.

FIG. 11A shows the pharmacokinetics of $LTB_4$ following i.j. administration at the dose of 50 µg/kg in rats. The data show that plasmatic $LTB_4$ concentration rapidly increases in rat following i.j. injection, reaching a maximum level 5 minutes after i.j. administration; the data also show that $LTB_4$ plasma levels return to baseline levels 30 minutes after i.j. administration. These data clearly show that $LTB_4$ is efficiently transferred from the jejunum into the peripheral circulation. FIG. 11B provides a comparison of the area under the curve (AUC) (for LTB4 plasma concentration) for the three different routes of administrations. In this case, the pharmacokinetic parameter AUC indicates the systemic exposure to the drug. As expected, $LTB_4$ administered directly into the circulation (i.v injection) resulted in the highest AUC. However, these data also clearly show that the AUC for the i.j. injection of $LTB_4$ is as high as 35% of that of i.v. $LTB_4$, demonstrating that upon i.j. administration, the uptake of $LTB_4$ in the circulation is efficient. These data further suggest that oral administration of $LTB_4$ using an appropriate formulation for delivery in the small intestine represents an efficient route for systemic administration of the drug. The AUC for s.c. administration of $LTB_4$ is shown for comparison purposes. Subcutaneous administration is known in the art to be an efficient way of administering $LTB_4$ in rat models.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A stabilized leukotriene $B_4$ ("$LTB_4$") agent pharmaceutical formulation comprising a therapeutically effective amount of leukotriene $B_4$[5S,12R-dihydroxy-6,8,10,14(Z,E,E,Z)-eicosatetraenoic acid]or a salt thereof, in association with a pharmaceutically acceptable aqueous carrier comprising less than 15% (vol/vol) acetonitrile at an alkaline pH between 8.2 and 14 effective to stabilize said $LTB_4$ agent, thereby increasing said formulation shelf-life for at least 3 months at 20° C.

2. The stabilized formulation of claim 1, wherein the formulation comprises only non-toxic substances.

3. The stabilized formulation of claim 1, wherein said alkaline pH ranges between 8.5 and 11.5.

4. The stabilized formulation of claim 1, wherein said alkaline pH ranges between 9.5 and 11.5.

5. The stabilized formulation of claim 1, wherein said aqueous carrier is selected from the group consisting of water, alkaline metal hydroxide solutions, buffered saline solutions, alcohol-containing aqueous solution, and sugar solutions.

6. The stabilized formulation of claim 5, wherein the alcohol of said alcohol-containing aqueous solution is selected from the group consisting of ethanol, propyleneglycol, benzyl alcohol, propanediol, glycerol, and mannitol.

7. The stabilized formulation of claim 1, wherein said carrier is a mixture of an organic solvent and water.

8. The stabilized formulation of claim 7, wherein said mixture comprises water and at least 50% (vol/vol) alcohol.

9. The stabilized formulation of claim 8, wherein said alcohol is selected from the group consisting of ethanol, propyleneglycol, benzyl alcohol, propanediol, glycerol, and mannitol.

10. The stabilized formulation according to claim 1, wherein said $LTB_4$ agent is leukotriene $B_4$[5S,12R-dihydroxy-6,8,10,14(Z,E,E,Z)-eicosatetraenoic acid] ("$LTB_4$").

11. The stabilized formulation according to claim 1, wherein said $LTB_4$ agent is present in amounts of from about 0.1 μg/ml to 25 mg/ml of the formulation.

12. The stabilized formulation according to claim 1, wherein said $LTB_4$ agent is present in amounts of from about 1 μg/ml to 1 mg/ml of the formulation.

13. The stabilized formulation according to claim 1, comprising less than 1% (vol/vol) acetonitrile.

* * * * *